United States Patent [19]

Gupta

[11] Patent Number: 5,055,300

[45] Date of Patent: Oct. 8, 1991

[54] TIME RELEASE PROTEIN

[75] Inventor: Kashmiri L. Gupta, San Clemente, Calif.

[73] Assignee: Basic Bio Systems, Inc., Missoula, Mont.

[21] Appl. No.: 362,034

[22] Filed: Jun. 5, 1989

Related U.S. Application Data

[62] Division of Ser. No. 208,731, Jun. 17, 1988.

[51] Int. Cl.⁵ .................. A01N 25/08; A23J 1/00
[52] U.S. Cl. .................. 424/409; 424/491; 424/499; 424/488; 424/489; 424/484; 424/485; 424/497; 426/656
[58] Field of Search .............. 424/491, 499, 488, 489, 424/484, 485, 497, 409; 426/656; 514/963

[56] References Cited

U.S. PATENT DOCUMENTS

| | | | |
|---|---|---|---|
| 2,828,206 | 3/1958 | Rosenberg | 424/491 |
| 2,895,829 | 7/1989 | Feo | 449/49 |
| 2,937,091 | 5/1960 | Rosenberg | 424/491 |
| 2,973,266 | 2/1986 | Rosenberg | 414/491 |
| 3,116,206 | 12/1963 | Brynko et al. | 424/491 |
| 3,137,631 | 6/1964 | Solloway | 424/491 |
| 3,390,050 | 6/1968 | Speiser | 424/497 |
| 3,496,272 | 2/1970 | Kruger | 514/182 |
| 3,516,941 | 7/1966 | Matson | 428/402.21 |
| 3,663,687 | 5/1972 | Evans | 424/499 |
| 3,720,534 | 3/1973 | Macaulay et al. | 428/321.3 |
| 3,786,123 | 1/1974 | Katzen | 424/491 |
| 3,886,084 | 5/1975 | Vassiliades | 428/402.22 |
| 3,985,298 | 12/1976 | Nichols | 239/54 |
| 3,989,649 | 11/1976 | Kaiho et al. | 521/29 |
| 4,089,848 | 5/1978 | Bell | 530/372 |
| 4,110,529 | 8/1978 | Stoy | 528/491 |
| 4,147,767 | 4/1979 | Yapel, Jr. | 424/499 |
| 4,154,728 | 5/1978 | Oughton | 530/372 |
| 4,208,259 | 6/1980 | Oughton | 204/180.1 |
| 4,208,260 | 6/1980 | Oughton | 204/183.1 |
| 4,211,695 | 7/1980 | Oughton | 530/372 |
| 4,211,801 | 7/1980 | Oughton | 426/430 |
| 4,230,687 | 10/1980 | Sair et al. | 426/72 |
| 4,232,047 | 11/1980 | Sair et al. | 426/656 |
| 4,307,201 | 12/1981 | Won et al. | 521/64 |
| 4,322,311 | 3/1982 | Lim et al. | 264/4.7 |
| 4,324,683 | 4/1982 | Lim et al. | 264/4.3 |
| 4,353,809 | 12/1982 | Hoshi et al. | 264/4.7 |
| 4,353,888 | 12/1982 | Sefton | 424/424 |
| 4,353,962 | 12/1982 | Himel et al. | 428/407 |
| 4,366,310 | 12/1982 | Leslie | 424/488 |
| 4,388,352 | 6/1983 | Allan et al. | 427/391 |
| 4,391,909 | 7/1983 | Lim | 435/178 |
| 4,396,670 | 8/1983 | Sinclair | 428/321.5 |

(List continued on next page.)

FOREIGN PATENT DOCUMENTS

| | | |
|---|---|---|
| 0171457 | 2/1986 | European Pat. Off. |
| 57-106610 | 7/1982 | Japan .................. 424/499 |
| 57-3212 | 3/1976 | Switzerland . |
| 573212 | 3/1976 | Switzerland . |

OTHER PUBLICATIONS

Coe et al, "New Nat. Ingred. for Cosmetic Formulators" D&CI/Sep. 73, pp. 48–56.

Elliott P. Barrett, et al., *The Journal of the American Chemical Society*, vol. 73, pp. 373–380 (1951).

Stephen Brunauer, et al., *The Journal of the American Chemical Society*, vol. 60, pp. 309–319 (1938).

Sheehan, and Thess, *The Journal of the American Chemical Society*, Vol. 77, p. 1067 (1955).

Voutsinas, and Nakai, J. Food. Sci. vol. 44, p. 1205 (1979).

*Primary Examiner*—Thurman Page
*Assistant Examiner*—William E. Benston
*Attorney, Agent, or Firm*—Knobbe, Martens, Olson & Bear

[57] ABSTRACT

Disclosed is a porous protein particle for delivering over a period of time an active ingredient impregnated therein, and methods of making and using the same. The protein particles have a median size less than about 50 microns. Active ingredient entrapped in the porous structure is gradually released from the protein particle.

11 Claims, 4 Drawing Sheets

ETHANOL ELUTION FROM PROTEIN CONCENTRATES

U.S. PATENT DOCUMENTS

| | | | |
|---|---|---|---|
| 4,401,456 | 8/1983 | Connick, Jr. | 71/88 |
| 4,407,841 | 10/1983 | Boocock | 426/618 |
| 4,407,957 | 12/1983 | Lim | 435/104 |
| 4,439,488 | 3/1984 | Trimnel et al. | 428/402.24 |
| 4,444,699 | 4/1984 | Hayford | 264/4.7 |
| 4,464,271 | 8/1984 | Munteanu et al. | 252/8.6 |
| 4,518,580 | 5/1985 | Pasarela | 424/410 |
| 4,522,953 | 6/1985 | Barby et al. | 521/64 |
| 4,576,826 | 3/1986 | Liu et al. | 426/289 |
| 4,581,378 | 4/1986 | Lazar et al. | 424/84 |
| 4,615,880 | 12/1986 | Loth et al. | 424/75 |
| 4,690,682 | 9/1987 | Lim | 424/491 |
| 4,690,825 | 9/1987 | Won | 521/63 |
| 4,707,355 | 11/1987 | Wilson | 424/84 |
| 4,828,836 | 5/1989 | Elger et al. | 424/464 |

ELUTION OF ENCAPSULATED ETHANOL
FRACTION I VS. FRACTION II

Fig. 1

ELUTION OF ENCAPSULATED ISOPROPANOL
1.0 G. FRACTION I, 0.79 G. ROH

Fig. 2

ELUTION OF ENCAPSULATED ACETONE
1 G. FRACTION 1, 0.75 G. ACETONE

Fig. 3

ETHANOL ELUTION FROM PROTEIN CONCENTRATES

Fig. 4

TIME RELEASE PROTEIN

This application is a division of application Ser. No. 208,731, filed 6/17/88.

BACKGROUND OF THE INVENTION

The present invention relates to vehicles for delivering an active ingredient, and more particularly, to vehicles which release the active ingredient over a prolonged period of time.

Controlled release of an active ingredient over time has significant advantages in numerous applications over one or more bolus releases of the active ingredient. Sustained release over an extended period of time enables application of a lower overall dose of the active ingredient while minimizing wide concentration gradients which result from multiple bolus applications. For example, in the case of a cream having dermatologic activity, a greater than necessary concentration of the active ingredient must often be applied due to various factors such as dilution due to perspiration, UV-initiated degradation, or volatilization which reduce its efficacy. Thus, the concentration of the active ingredient may start out much higher than necessary, implicating toxic dose or allergy considerations, then decline through and below the effective dosage range. Flattening the dosage curve and extending the delivery time thereof through the use of time release vehicles can achieve significant advantages in many fields, including medicine, cosmetics, pesticides, herbicides, fertilizers and others.

Known time release vehicles generally fall into one of several categories. A first type of carrier comprises beads or droplets of active ingredient encapsulated in a polymeric coating designed to solubilize or rupture under predetermined circumstances to release the active ingredient. This first type of microencapsulation generally provides a bolus release of the active ingredient upon the occurrence of the predetermined event to rupture the membrane. For example, U.S. Pat. No. 3,786,123 to Katzen discloses encapsulation of nutrients in a high protein content vegetable composition which solubilizes in the environment of the digestive tract.

Another known microencapsulation technique, which achieves a more prolonged release of active ingredient over time, utilizes a microencapsulation coating or membrane which is either semi-permeable or porous to allow the active ingredient to diffuse out of the microcapsule.

A third type of vehicle comprises a porous matrix having an active ingredient dissolved or dispersed throughout. The delivery rate of the active ingredient is a function of the porosity of the structure, the solubility of the active ingredient, and other driving forces such as diffusivity responsible for liberating the active ingredient from the matrix. For example, U.S. Pat. No. 4,690,825 to Won discloses a time release delivery vehicle comprising a spherical polymeric bead having a network of pores with an active ingredient held within the network to provide controlled release of the active ingredient.

For some applications, however, the synthetic polymer bead carriers are disadvantageous. Microencapsulation in a polymeric bead or shell is typically achieved by adding the active ingredient to a monomer solution prior to or during the polymerization step. As the porous polymer structure is formed, active ingredient is entrapped within the pores. It is also possible that excess monomer can be trapped within the pores to be released with the active ingredient. The presence of monomer presents a potential health hazard. Synthetic polymer microencapsulation vehicles typically have the further disadvantage of imparting an undesirable gritty feel to topical creams mad up for cosmetic and dermatologic applications. Regardless of the application, synthetic polymers used for microencapsulation are generally not biodegradable. Therefore, these polymers may not be used in powder forms if there is a possibility of inhalation. A small nondegradable particle, if inhaled, can present the possibility of serious health consequences if it remains in the body. In addition, some synthetic polymers can decompose to give off hazardous chemicals under certain circumstances. These problems limit the usefulness or detract from the desirability of synthetic polymers in a number of applications.

SUMMARY OF THE INVENTION

To overcome the foregoing disadvantages of prior art synthetic bead and shell delivery vehicles, there has been provided in accordance with one aspect of the present invention a time release delivery vehicle for delivering an active ingredient over time, which comprises a multiplicity of biodegradable porous protein particles, each having a network of pores with the active ingredient contained therein. The protein particles are usually irregular in shape, and are derived from natural grains and legumes such as canola, beans, oats, rapeseed and soya. In addition, the particle size is generally between about 1/10 micron to 50 microns. The porous delivery vehicle can further be provided with an outer encapsulating layer to prevent escape of any of the active ingredient from the pores of the delivery vehicle, until exposure to a predetermined triggering agent or event which will remove or render permeable the outer layer. Such an event could be a change in temperature or pH, exposure to ultraviolet light, or exposure to a solvent for the active ingredient such as perspiration.

In accordance with another aspect of the present invention, there has been provided a process of preparing a time release delivery vehicle for delivering an active ingredient over time. According to the process, a biodegradable protein concentrate (such as seed protein) having a porous structure is provided, and indigenous volatiles such as moisture are removed from the particulate to form a substantially dry powder. In most applications, the dried powder obtained after the removal of indigenous volatiles is then combined with the active ingredient under agitation so that the active ingredient will permeate the porous structure of the powder. The active ingredient may be dissolved in a suitable solvent, which solvent is removed later after impregnation of the particles with the active ingredient. The removal of solvent may not be necessary for some applications. An example of such a situation is entrapment of water, or an active ingredient dissolved in water.

The indigenous volatiles may be removed by any of a variety of known methods such as heating and/or vacuum drying, or removal by solvent extraction. The dried powder may then be combined with the active ingredient in any of a number of known ways, such as in a tumble dryer or using spouted bed or fluidized bed or spraydrying techniques. The resulting impregnated powder may be used dry, or be formulated into an emulsion or suspension with a medium suitable for any of a variety of cosmetic, pharmaceutical, or insecticide applications.

In accordance with a further aspect of the present invention, there has been provided a method of delivering an active ingredient over time, which includes the steps of providing a porous protein particle having an active ingredient therein and permitting the active ingredient to migrate out of the pores to provide a sustained release of the active ingredient. Commencement of the migration step can be made responsive to the occurrence of an enabling event which increases the solubility or diffusivity of the active ingredient. These events may occur at the application site as a result of change of one or more factors such as pH, temperature, moisture content, or mechanical perturbations.

Further features and advantages of the present invention will become apparent from the detailed description of preferred embodiments which follows.

DETAILED DESCRIPTION OF PREFERRED EMBODIMENTS

Figure 1:
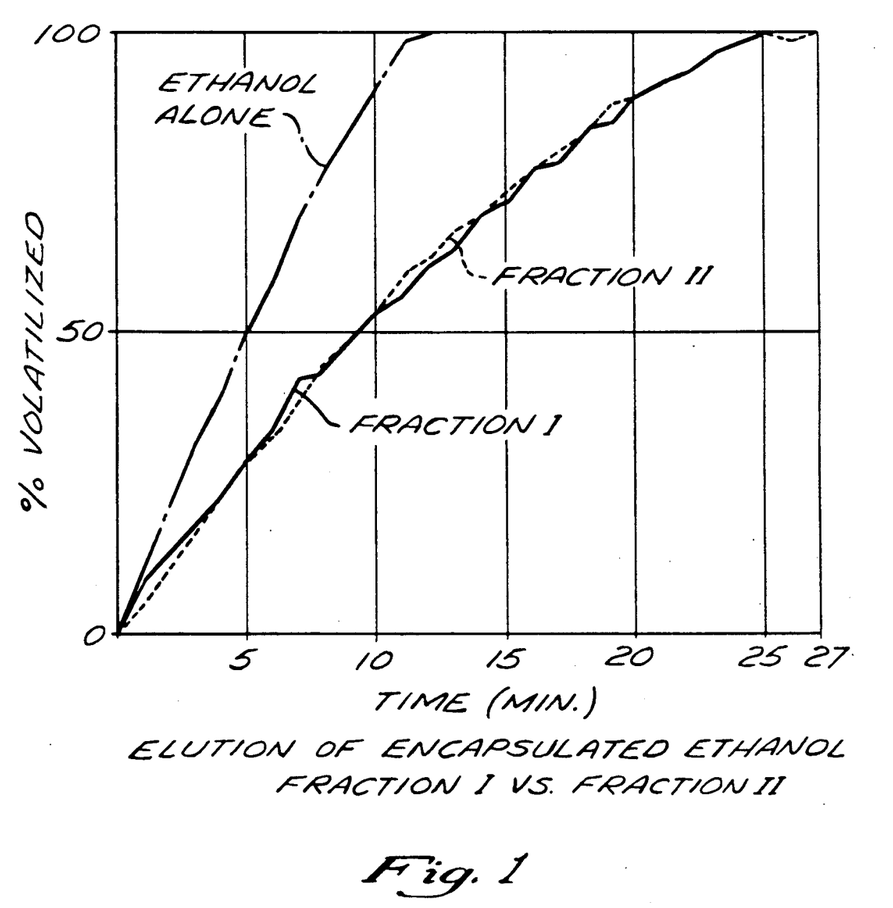
FIG. 1 is a graph comparing evaporation rates of ethanol with encapsulated ethanol.
Figure 2:
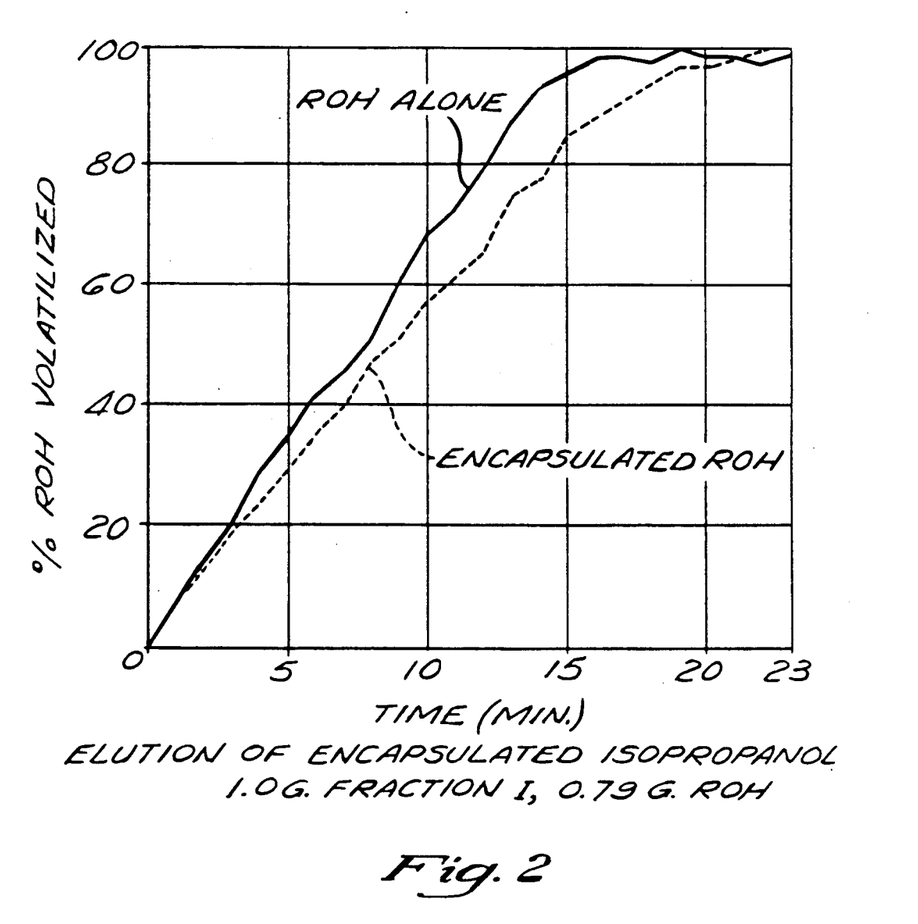
FIG. 2 is a graph comparing evaporation rates of isopropanol with encapsulated isopropanol.
Figure 3:
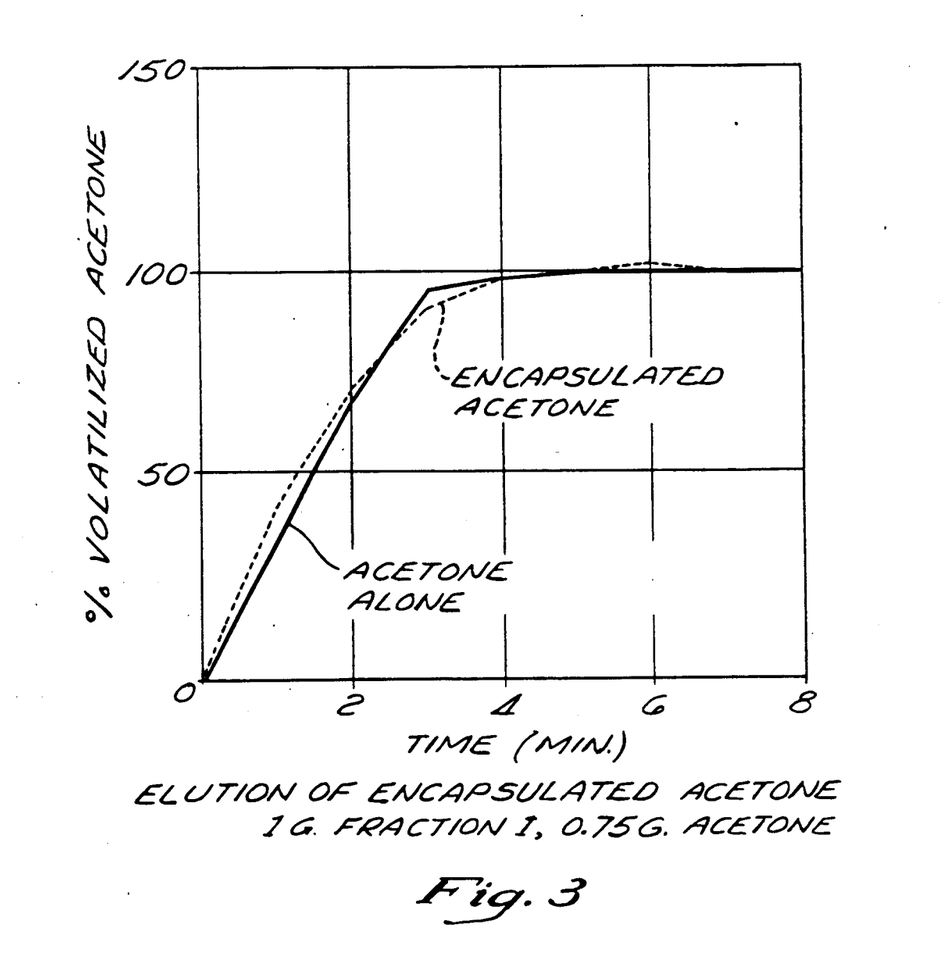
FIG. 3 is a graph comparing evaporation rates of acetone with encapsulated acetone.
Figure 4:
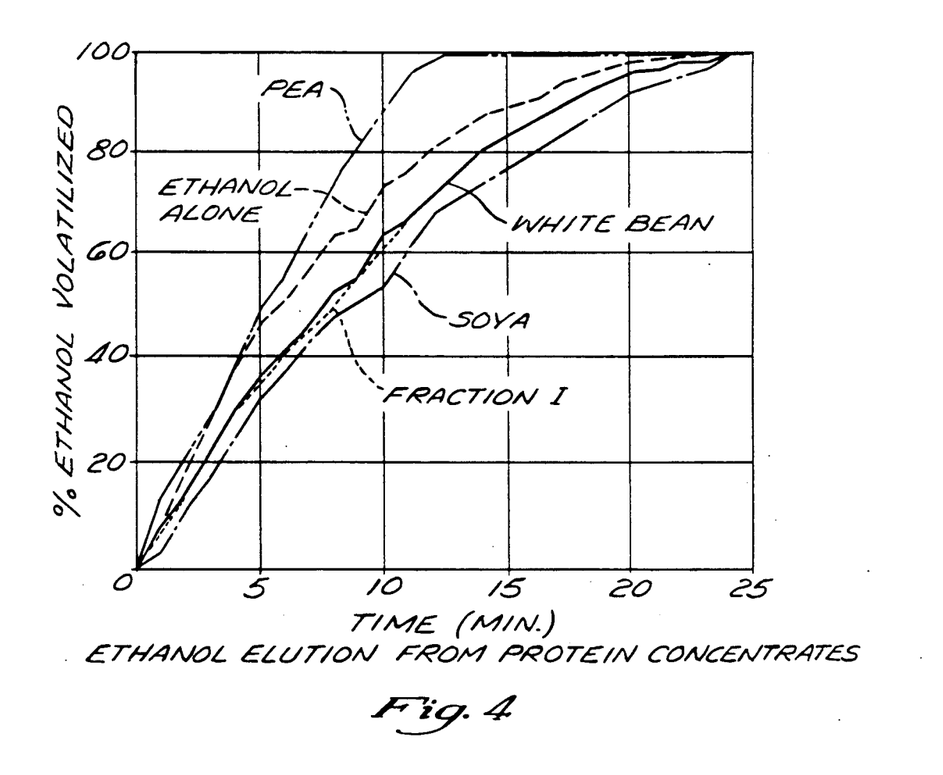
FIG. 4 is a graph comparing ethanol elution rates of four different impregnated protein concentrates.

The present invention provides a porous protein delivery vehicle for delivering an active ingredient over a prolonged period of time. The protein concentrate for use in the present invention comprise natural proteins. Preferred proteins are derived from grains or legumes such as canola, beans, oats, rapeseed, and soya.

A number of known processes exist for the preparation of a suitable protein powder for use in the present invention. For example, in U.S. Pat. No. 4,089,848 to Bell, the isolation of a proteinaceous fraction from oats is disclosed by extracting lipids from the comminuted oats with an organic solvent, carrying out alkaline and acid precipitation on the residue, and finally isolating the acid soluble protein. Oughton, in U.S. Pat. No. 4,154,728, describes another process for separating fractions of differing compositions from comminuted proteinaceous material from a variety of food sources including wheat, rye, barley, triticale, peas and buckwheat. The Oughton process comprises mixing the proteinaceous material with an aliphatic hydrocarbon or alcohol suitable to dissolve the lipids in the material. The wet slurry is distributed by means of centrifugation into fractions which differ primarily in protein composition. A similar process is applied to comminuted oats in U.S. Pat. Nos. 4,211,695 and 4,211,801 to Oughton.

To facilitate recovery of the protein in powder form from the slurry produced in accordance with the foregoing processes, U.S. Pat. Nos. 4,208,259 and 4,208,260 to Oughton disclose the application of an electric field to the mixture and collection of a comminuted oat fraction which clings to the anode. An improved method of recovery is disclosed in U.S. Pat. No. 4,407,841 to Boocock, comprising the addition of aqueous ethanol to the slurry to agglomerate the proteinaceous material and facilitate separation thereof.

The protein particles are separated to an approximate median particle size of less than 50 microns, and to as fine as 0.1 micron or less depending upon the desired end use of the carrier. For example, a larger particle size (and therefore a larger total pore volume and surface area) can result in a longer period of sustained release.

Because the powder is derived from natural grains and legumes, the particles will be irregular in shape, due to crushing and fragmenting during the milling process. However, median particle size can be determined by milling parameters or by using a series of graduated sieves or particle size analysis. Also because of their natural origin, the protein particles of the present invention are fully biodegradable, and there is no possibility of entrapped unreacted monomer to chemically interact with or be released with the active ingredient, nor are there harmful polymer degradation products that could be released.

Many suitable protein concentrates or protein powders are commercially available. For example, soya protein concentrate is available in 96% pure form from Protein Technologies International, St. Louis, Mo., U.S.A. Great Northern White Bean protein concentrates are available from POS, Ltd., Saskatoon, Canada.

Several advantages are accrued through the use of a fine particulate of naturally occurring grain or seed proteins over prior art time release carriers. The protein particles of the present invention are typically smaller in size than the prior art synthetic polymer beads, and the protein particles are also somewhat resilient, whereas the synthetic porous beads known in the art are relatively rigid structures. As a result, creams and emulsions formulated using the carrier of the present invention exhibit an exquisitely smooth feel, compared to the gritty texture imparted by prior art porous beads. This is a particularly important feature for certain applications of the time release carrier, such as inclusion in formulations intended for cosmetic or dermatologic use.

The protein concentrate is advantageously dried prior to use as a carrier according to the present invention, to remove water and other indigenous volatiles which may otherwise reduce the available pore volume necessary for holding the active ingredient. In addition, depending upon the protein separation process, residual solvent could reside in the pores which could react adversely with the active ingredient.

Drying can be accomplished by any of a number of known methods, such as oven drying at elevated temperatures or subjecting the powder to a vacuum with or without the addition of heat. Alternatively, solvent extraction methods can be used, depending upon the particular requirements of the active ingredient and the end use of the carrier.

The dried protein concentrate is then impregnated with any of a variety of active ingredients which are desired for release over a prolonged period of time. The particular active ingredient to be used can vary widely, including such diverse applications as in cosmetics, pharmaceuticals, and insecticides. Volatiles can be entrapped, such as alcohol and various fragrance compounds. Various ingredients in cosmetics are suitable for entrapment, such as para amino benzoic acid (PABA) or its derivatives and PARSOL (a trademark of Bernel Chemical Company) or other active sunscreen ingredients, as well as moisturizing ingredients such as urea and mineral oil. Numerous dermatologically active materials are suitable for entrapment in the carrier of the present invention, including benzoyl peroxide, resorcinol and retinoic acid for acne, and a variety of deodorants. Additional pharmaceutically active ingredients can include antibiotics, fungicides, astringents, anti-inflammatory agents and antipruritics. Insecticides such as pyrethrins for flea control on pets can be entrapped in the carrier of the present invention, as well as numerous agriculturally related compositions such as herbicides, fungicides, fertilizers and insecticides. The foregoing are only illustrative of a few of the many ingredients that can be utilized with the protein particles of the present invention.

The quantity of the active ingredient to be entrapped will vary depending upon the desired dosage of active ingredient to be delivered in terms of either total volume or total elapsed delivery time, the viscosity and/or volatility of the active ingredient, and other parameters that will be apparent to one of skill in the art. Entrapped active ingredient can reach as high as 50% by weight of the solids, or more.

Entrapping or encapsulating the protein concentrate with an active ingredient may be accomplished by any of a variety of methods which can be envisioned by one of ordinary skill in the art. For example, the active ingredient may be sprayed into the powder in a liquid mist form while the powder is maintained in constant motion. The necessary motion can be achieved in any of a variety of commercially available tumble dryers or other equipment designed for agitating a powder. In addition, spouted bed dryers, fluidized bed dryers or other equipment which will be appreciated by one skilled in the art can be used. Alternatively, the active ingredient can be dissolved in a suitable solvent and the protein particles immersed in the resulting solution with or without agitation. The introduction of many active ingredients into the porous structure of the protein powder can be facilitated by performing the introduction step at elevated temperatures.

It is further anticipated that some nonactive ingredients such as surfactants (e.g. polysorbates) and cosolvents (e.g. alcohols) may be encapsulated to modify the release rates of the active ingredient. The change in release rates may be due to emulsification or dissolution of the active ingredient.

After sufficient active ingredient has permeated the structure of the protein powder, the agitation can be ceased and the material cooled. If a solvent was used to carry an active ingredient into the protein particle, that solvent can be evaporated by heating or exposing to a vacuum, or both, depending upon the thermal stability of the active ingredient.

The delivery vehicle of the present invention can be designed to commence the period of timed release of the active ingredient upon the occurrence of any of a variety of enabling events. This is useful to ensure an acceptable shelf life for the commercial product. For example, an active ingredient may solubilize when contacted with perspiration or other body fluid, in which case the solubility may become a part of the rate determining step. Alternatively, an active ingredient may solubilize or volatilize in response to a change in temperature or pH.

In a variation of the delivery vehicle of the present invention, an outer layer is provided to encapsulate the impregnated protein particle with an impermeable membrane, which may comprise either a solid or a liquid. In this embodiment, the period of controlled release will not commence until the membrane has been ruptured or dissolved. After the rupture or compromise of the outer membrane, the active ingredient will diffuse out of the delivery vehicle in the manner described supra. For example, a water soluble membrane may be formed by coating the particle with an aqueous solution of polyvinyl alcohol, and then drying to form a film.

Another encapsulation technique is disclosed in U.S. Pat. No. 3,786,123 to Katzen. Katzen discloses the encapsulation of an active ingredient in gelatinized corn flour. According to that method, the active ingredient was thoroughly admixed with the corn flour and the resulting admixture was extruded in an extruder manufactured by the Wenger Mixer Manufacturing Company of Sabetha, Kans. The extruder was operated at a pressure of 1,000 psi and a temperature of 240° F. This temperature was selected as sufficient to gelatinize the corn flour yet not deleteriously affect a selected active ingredient. The gelatinized corn flour completely enclosed individual or groups of particles of the active ingredient.

By utilizing this or another known encapsulation method, attributes of both the porous matrix and the microencapsulation systems can be combined. This is particularly useful, as described, when a certain shelf life or other prolonged period will be necessary before the active ingredient will be put to use.

Modification of Proteins

Several methods are available to modify the protein concentrate. These methods have been generally developed by protein chemists for peptide synthesis. These reactions are generally limited to carboxyl and amino groups in the alpha position. One such well-known method is that of Sheehan and Hess, J.Am.Chemical Soc. 77:1067 (1955). According to this method, the carboxyl group of the protein is activated by a water soluble carbodimide such as 1-ethyl-3-(3-dimethylaminopropyl) carbodimide. The carbodimide-activated intermediate is reactive. The activated group can be further reacted with methionine and tryptophan. Processes for using these modifications of soya protein are known and are described by Voutsinas and Nakai, J.Food Sci. 44:1205 (1979).

The carbodimide method and other protein derivitization methods can be used to attach molecules that affect the release rates of the active ingredient. Of course, the particular molecule attached will depend on characteristics of the active ingredient and the desired release profile. For example, lipid-type materials may be attached to slow the release of lipophilic active ingredients. Hydrogen bonding characteristics may also be used to slow release of appropriate active ingredients by attaching molecules to which the active ingredient will hydrogen bond. Ligand or chelating derivitizing molecules capable of releasably binding the active ingredient are similarly contemplated.

Protein concentrates modified by these methods can be used not only to tailor the rate of release, but also to achieve the necessary aesthetics for cosmetic and dermatological applications.

Alternatively, a delivery vehicle can be provided having a permeable outer membrane which will operate in addition to the porous protein structure as a further rate limiting structure. A number of membranes are feasible. These can range from an oil layer on the surface of the particles to surface coatings formed from polymers such as Polyvinyl alcohol, polyacrylates, and polysaccharides such as Dextran, Guar, Gum Arabic, etc. Some of these reagents may also be dispersed within the particles.

Selection of a particular outer membrane, whether permeable or nonpermeable, will likely be influenced by the intended use of the system. For example, in some pharmaceutical applications, an outer membrane will be selected which will impart desirable suspension characteristics, without introducing toxic or adversely reactive solvents.

The dried impregnated protein powder, with or without an encapsulating layer, can then be mixed with any of a variety of creams, gels, oils, lotions, or other media to form mixtures, emulsions or suspensions for cosmetic, pharmaceutical or other products. The powder can be mixed with other dry ingredients such as fillers and stabilizers if it is desired that the end product be delivered in dry form. Any of a variety of known pharmacologically acceptable excipients may additionally be utilized as the delivery medium for the impregnated powder.

Accordingly, the protein particle carrier of the present invention can be incorporated into any of a vast variety of media for bringing the impregnated particle into communication with the surface where the active ingredient is to be released. In the case of a medium having a solvent base, such as any of the creams, gels, oils, lotions, or other "wet" media, it is often desirable that the active ingredient be insoluble in the solvent of the media. In this manner, the active ingredient will not commence to discharge from the porous protein particle simply by virtue of its contact with the delivery medium. For example, in the case of a sunscreen application of the present invention, an active ingredient which is soluble in water and, hence, in perspiration, would optimally be incorporated into a cream or a lotion which is not water-based. If a water-based medium is nonetheless desirable for other reasons, then the protein particle can be encapsulated in an outer impermeable membrane which is designed to rupture or compromise under circumstances other than mere exposure to an aqueous environment.

Encapsulation and Release Rate Data

A number of active ingredients have been encapsulated using protein concentrates. The maximum amount of material entrapped depends on the characteristics of the active ingredient. In general, the maximum amount of active ingredient has been around 40% by weight of the dry solids. The experimental values for maximum loading are shown in Table 1. These ingredients are fully extractable with solvents.

TABLE 1

| Ingredient | Maximum Loading Wt % Active Ingredient |
|---|---|
| Mineral Oil | 40 |
| Parsol-MCX | 40 |
| Pyrocide Technical 5192 | 40 |

Note: Parsol-MCX was obtained from Bernel Chemical Company of Engelwood, New Jersey.
Pyrocide Technical 5192 was obtained from MGK of Minneapolis, Minnesota.
Protein Concentrate from oats was used for this study.

The release rates from the particles are a function of the ingredients and the environment. The active ingredient can be released as a result of vapor diffusion to the atmosphere, liquid and/or vapor diffusion to surfaces such as skin and release due to chemical interaction or dilution. At present the experimental data is limited to vapor diffusion to the atmosphere. However, other studies are planned.

The release rates of volatile materials such as alcohols and solvents have been studied. Organic materials such as ethanol, isopropyl alcohol, butanol and acetone were used for this work. Three sources of protein concentrates have been used. The protein concentrates from Peas and Great Northern White Beans were obtained from POS, a contract research center in Saskatoon, Canada. Soya concentrate (PP660) containing 92% protein was obtained from Protein Technologies International of St. Louis, Mo. A protein concentrate from oats was prepared in our laboratory. The release rates were studied at room temperature, which was controlled around 22° C.

In all cases, a 1 gram sample of protein concentrate was mixed with 1 gram of organic material such as ethanol, acetone, etc. in an open glass petri plate (5 cm.). One gram of the organic material was also added to another similar petri plate. Both petri plates were left open to the atmosphere. The room temperature during these experiments was about 22° C. Each plate was weighed every few minutes using a Mettler PE1600 balance. The weight loss was calculated as a function of time. In some cases more than one solid was used for encapsulation. Even in these cases, the weight changes for the encapsulated material and the control were determined concurrently. This ensured uniformity of operating conditions.

The experimental data are represented graphically in FIGS. 1 to 4. In these graphs, the fractions I and II refer to protein concentrates from oats. The data show that the release rate is dependent on the ingredient encapsulated. The major effect on release rates is for the organics such as alcohols with reactive groups capable of forming significant association with carboxyl and/or amino groups of the proteins. The release rates are not significantly affected for solvents such as acetone, which do not form any significant association with protein particles under the atmospheric conditions. However, acetone release rates may be affected by modifying the structural properties of proteins in the concentrates. FIG. 4 indicates that the release rates are affected by the concentration of protein and its origin.

For the purpose of illustration, and not in any way to limit the applicable scope of the present invention, reference is made to the following examples.

The examples use a number of protein concentrates obtained from a research center (POS, Saskatoon, Canada) and International Protein Technologies of St. Louis, Mo. These concentrates contained 50–90% protein by weight. The particle size of these concentrates ranged from less than 1 micron to 10 microns. A protein concentrate from oats was prepared in our laboratory.

Example 1—Sunscreen Lotion

PARSOL is a popular sunscreen chemical available from Bernel Chemical Company, Engelwood, N.J., and used in the preparation of sunscreen lotions. The maximum concentration of PARSOL is generally limited to about 6% by weight to minimize any allergic reactions. Entrapment of PARSOL in accordance with the present invention can reduce the concentration of the chemical in direct contact with the skin at any one time, yet permit an effective amount of the sunscreen agent to be present at any time during the active life of the lotion. Moreover, the active ingredient can be more stable in entrapped form, and absorption by the skin will be reduced. All of these factors will provide a sunscreen lotion which is more effective, longer lasting, and resulting in reduced skin irritation.

Extracted oat protein concentrate was prepared which was relatively free of any lipids and contained up to 40% protein. The protein concentrates were further dried in a convection oven for two hours at about 45°-50° C. This procedure ensured that the protein concentrates were substantially free of volatile compounds such as water.

A 16-gram sample of PARSOL was weighed out into a beaker and mixed with 16 grams of isopropyl alcohol to fully dissolve the PARSOL. A 40-gram sample of oat protein concentrate was thereafter mixed with the alcohol-PARSOL mixture. The resulting mixture was homogenized by manual stirring for approximately 20 minutes, and was allowed to stand for an additional 30 minutes to ensure uniform penetration. The solvent was allowed to evaporate under a hood until a free flowing powder was obtained. The final powder contained about 30% PARSOL by weight. This powder was used to prepare a sunscreen lotion by combining it with mineral oil and isopropyl palmitate. Encapsulated powder showed better stability against UV light compared to PARSOL.

Example 2—Sunscreen Lotion

The experiment described in Example 1 above was repeated, using a protein concentrate from Great Northern White Bean. This experiment again resulted in a freeflowing powder impregnated with PARSOL, which was used to make a sunscreen lotion.

Example 3—Flea and Tick Powder

Synergized pyrethrins are a common active chemical used for control of fleas on dogs. Pyrethrins are generally synergized with piperonyl butoxide. One such synergized material is marketed by McLaughlin Gormley King ("MGK") of Minneapolis, Minn. However, these chemicals have unpleasant smells and the life of the chemicals is relatively short after application.

Protein concentrate as described above was first dried in a convection oven for two hours at about 80°-90° F. to remove most of the volatile components. A 4 gram sample of MGK pyroside intermediate 5192 was mixed with 6 grams of isopropyl alcohol. This mixture was thoroughly mixed for 30 minutes with the protein concentrate to allow permeation of the alcohol-pyroside intermediate 5192 mixture into the porous structure of the protein. The alcohol was thereafter allowed to evaporate while the mixture was continually stirred to maintain uniform dispersion of the active ingredient. The resulting powder showed much reduced odor. In addition, a test conducted at the University of California, Riverside indicated that the material is effective in extermination of roaches and fleas. The encapsulated pyrethrin showed better stability against UV light compared to unencapsulated pyrethrin.

Example 4—Insecticide

Dursban is the trademark for an insecticide marketed by Dow Chemical Company. The major use of this chemical is for the environmental control of insects and roaches, and the chemical is characterized by a strong, unpleasant odor. Thus, Dursban was impregnated into the porous structure of a protein powder to reduce the odor while at the same time allowing a continuous effective release of the active ingredient.

A powdered protein concentrate from oats of the type previously described was allowed to dry in a convection oven at about 80°-90° .F for about two hours. A 0.25-gram sample of Dursban was weighed into a beaker and mixed with 6 ml chloroform to fully dissolve the solids. A 100 gram sample of protein concentrate was thereafter introduced into the chloroform-Dursban solution under constant agitation to impregnate the protein concentrate. The mixture was stirred for 30 minutes at room temperature. Chloroform was thereafter allowed to evaporate under a hood while the mixture was maintained under constant agitation until a dry powder was obtained. The dried material was a freeflowing powder showing only faint odor, and it was found to be effective in killing German roaches. Moreover, the protein concentrate itself showed significant insecticidal activity. This may be due to disruption of the insects' protective cuticle layer.

Although this invention has been described in terms of certain preferred embodiments, other embodiments and applications that are apparent to those of ordinary skill in the art are also within the scope of this invention. Accordingly, the scope of the invention is intended to be defined only by reference to the appended claims.

What I claim is:

1. A time release delivery vehicle for delivering an active ingredient, comprising a multiplicity of discrete natural, unhydrolyzed seed protein particles in powder form from which lipids naturally found in said seeds have been separated, each said particle having a network of pores with the active ingredient impregnated into the pores of said particles in such a manner that the active ingredient can migrate out of said pores in a controlled manner to release active ingredient over a period of at least 20 minutes.

2. A time release delivery vehicle as in claim 1, wherein the protein particles are biodegradable.

3. A time release delivery vehicle as in claim 1, wherein the protein particle is derived from natural grains or legumes.

4. A time release delivery vehicle as in claim 1, wherein the protein particles are of irregular shape.

5. A time release delivery vehicle as in claim 3, wherein the grain or legume is selected from the group consisting of canola, beans, oats, rape seed, soya, peas, and wheat.

6. A time release delivery vehicle as in claim 1, wherein the median particle size is less than about 50 microns.

7. A time release delivery vehicle as in claim 1, further comprising an outer layer encapsulating the protein particles and having the active ingredient contained therein.

8. A time release delivery vehicle as in claim 7, wherein the outer layer is impermeable to the active ingredient.

9. A time release delivery vehicle as in claim 7, wherein the outer layer comprises a porous polymer.

10. A time release delivery vehicle as in claim 6, wherein the median particle size is within the range of from about 0.1 to 50 microns.

11. A time release vehicle as in claim 1, wherein amino or carboxyl groups or both, of the protein have been derivatized to alter the release characteristics of active ingredient from the release characteristics possessed by the protein particles in underivatized form.

* * * * *